United States Patent [19]
Giampapa

[11] Patent Number: 5,195,951
[45] Date of Patent: Mar. 23, 1993

[54] CHIN IMPLANT

[76] Inventor: Vincent C. Giampapa, 89 Valley Rd., Montclair, N.J. 07042

[21] Appl. No.: 674,394

[22] Filed: Mar. 25, 1991

[51] Int. Cl.$^5$ ............................................. A61F 2/28
[52] U.S. Cl. ...................................... 623/16; 623/66
[58] Field of Search ................ 623/11, 12, 16, 18, 623/8, 66

[56] References Cited

U.S. PATENT DOCUMENTS

| | | | |
|---|---|---|---|
| 3,257,668 | 6/1966 | Braley | 623/10 |
| 4,344,191 | 8/1982 | Wagner | 623/16 |
| 4,597,763 | 7/1986 | Schweilchart | 623/8 |
| 4,627,853 | 12/1986 | Campbell et al. | 623/16 |
| 4,731,082 | 3/1988 | Giunta | 623/10 |
| 4,888,018 | 12/1989 | Giampapa | 623/16 |

*Primary Examiner*—David Isabella
*Attorney, Agent, or Firm*—M. K. Silverman

[57] ABSTRACT

The implant for the chin is defined by a solid crescent formed by the intersection of an interior radius of curvature with an exterior radius of curvature in which the interior radius is slightly smaller than the exterior radius, the resulting crescent having a total included angle of approximately forty-five degrees. An outer portion of the implant is provided with a softer, lower durometer material than is the rest of the implant to simulate the fat pad at the point of the chin.

8 Claims, 1 Drawing Sheet

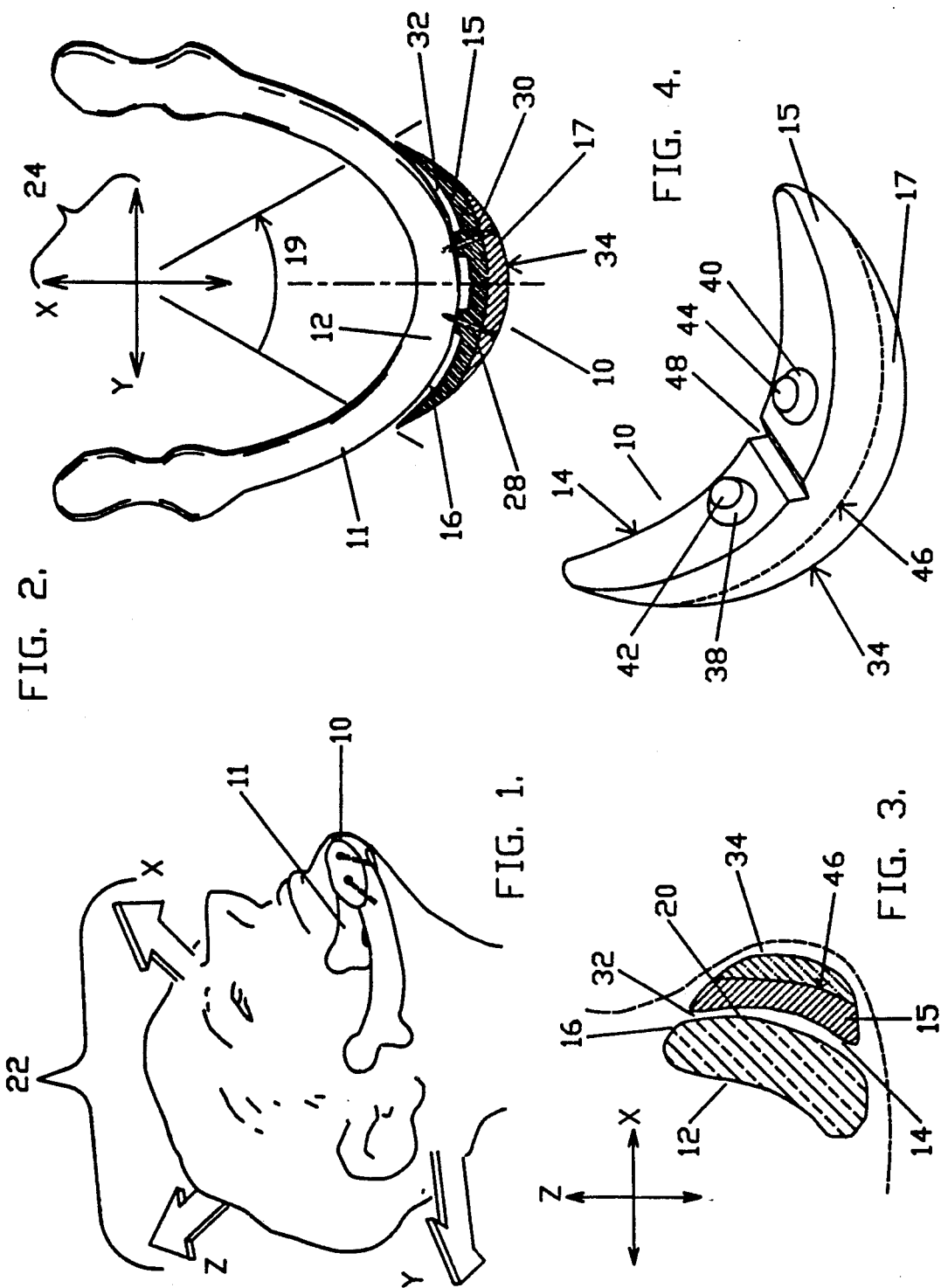

CHIN IMPLANT

BACKGROUND OF THE INVENTION

The present invention is directed to a chin implant for a human mandible and, more particularly, is an improvement of my invention as embodied in U.S. Pat. No. 4,888,018 (1989), entitled Method For Positioning and Securing a Chin Implant. The instant invention relates to an implant which is compatible for use with the method as taught in said patent.

Heretofore, chin implants of a resilient or silastic material (such as silicone) have been applied, during surgery, to the exposed mandible and retained in position by re-assembled skin tissue to enclose and engage the implant. One difficulty with this procedure, which is addressed by my above referenced patent, has been that during and after healing, such implants have been known to become mechanically displaced from the desired central location on the mandible. Also, in some instances, the pressure of the implant against the mandible has resulted in a re-absorption process of the silicone by the bone. This process is sometimes referred to as bone re-absorption and is due to a piezoelectric effect at the bone-implant interface.

The instant invention relates to an implant which reduces the bone-implant interface and, additionally, teaches the use of an implant, generally similar in geometry to the implant taught in my said U.S. Pat. No. 4,888,018, however, having a so-called dual durometer characteristic at the point of the chin, that is, in the outer surface of the mandible.

Other prior art respecting the present invention is U.S. Patent, is U.S. Pat. No. 3,720,959 (1973) to Hahn; U.S. Pat. No. 4,344,191 (1982) to Wagner; and U.S. Pat. No. 4,439,115 (1984) to Small. Related foreign references, know to me are French Patent No. 2,447,182 (1980) and USSR Patent No. 0637118 (1978).

None of the above, or other prior art known to me teaches a chin implant of the disclosed type capable of suspension above the periostium of the chin in the manner taught herein. Further, no prior art known teaches the use of a dual durometer pad, at the outward point of a prosthetic chin, to simulate the fat pad at the point of the chin.

SUMMARY OF THE INVENTION

The instant invention is a chin implant formed of a biologically inert material, such as silastic silicone, which is surgically inserted, between the periostium and the mandible and is positioned upon the outer surface of the mandible to form an ascertainable build-up of the jaw. The implant is defined by a solid crescent formed by the intersection of an interior radius of curvature with an exterior radius of curvature in which the interior radius is slightly smaller than the exterior radius, the resulting crescent having a total included angle of approximately forty-five degrees. An outer portion of the implant is provided with a softer, lower durometer material than is the rest of the implant to thereby simulate the fat pad at the point of the chin.

It is accordingly an object of the invention to provide a chin implant having the appearance and feel of a natural chin after surgical implantation has occurred.

It is another object of the invention to provide a chin implant, for use with menoplasty procedures, adapted for securement within the periostium of the chin.

It is a further object of the present invention to provide a chin implant of the above type which is provided, upon the surface thereof projecting away from the mandible, a portion consisting of a reduced durometer or softer, material to thereby simulate the appearance and texture of the fat pad of the human chin.

It is a still further object of the present invention to provide a chin implant which will minimize or eliminate the piezoelectric effect associated with bone adsorption at the implant-bone surface interface.

The above and yet other objects and advantages of the present invention will become apparent from the hereinafter set forth Brief Description of the Drawings, Detailed Description of the Invention, and Claims appended herewith.

BRIEF DESCRIPTION OF THE DRAWINGS

FIG. 1 is a perspective representational view showing the inventive implant upon the chin and, as well, showing an XYZ Cartesian coordinate system for the purpose of defining planes and axes of reference upon the anatomy of the chin and face.

FIG. 2 is a top cross-sectional view of the chin, mandible and implant taken along of the plane XY of FIG. 1.

FIG. 3 is a side cross-sectional view taken along the plane XZ the views of FIGS. 1 and 2.

FIG. 4 is a perspective view of the inventive implant.

DETAILED DESCRIPTION OF THE INVENTION

In regard to the views of FIGS. 1 and 2, there appears an XYZ Cartesian coordinate system which includes an XZ plane 22 which plane defines the front-to-rear vertical medial plane of the face. The system also includes a XY plane 24 which defines a front-to-rear horizontal plane at the level of the mandible 11 and chin 12 (physiologically the chin is a part of the mandible).

Further shown in FIGS. 2, 3 and 4 is a chin implant 10 which, in a preferred embodiment, consists of a so-called silastic material in the nature of a silicone. As is more fully described below, the implant is a solid crescent consisting of an outer radius 34 and an inner radius 14, in which an inner portion 15 is bonded to an outer portion 17 at interface 46. The solid included angle 19 in the XY plane shown in FIG. 2 is typically in the range of 30 to 65 degrees.

The silicone implant itself may either be preformed or sculptured employing the so-called hard slice method.

In FIG. 3, the implant 10 and chin 12 may be seen in cross-sectional view, that is, in the XZ plane. Shown in FIG. 3 is the periostium 20 of chin 12. The periostium is a soft elastic tissue which covers the boney exterior of the chin or mandible. As may be noted with reference to the views of FIGS. 3 and 4, inner portion 15 of implant 10 is provided with offsets 38 and 40, each having linear bores 42 and 44 respectively through which respective mounting pins 28 and 30 (see FIG. 2) may be past. As noted in the view of FIG. 4, said bores 42 and 44 start, at the outer ends thereof, at either side of outer XZ radius 34 of the outer portion 17.

As may be seen in FIG. 2, there is provided a crescent shaped offset 32 between interior radius 14 of inner portion 15 of implant 10 and chin 12 in which radius 14 is slightly smaller than the opposing radius of curvature 16 of the area of the chin 12 which is to receive said implant.

Thereafter, pins 28 and 30 are advanced through bores 42 and 44 respectively (see FIGS. 2 and 4) and into periostium 20 (see FIG. 3), penetrating the periostium to a depth between two and five millimeters. In the preferred embodiment, the axis of bore 42 is that of an outward angulation of about thirty degrees relative to the front-to-rear vertical median plane (the XZ plane) as is shown in FIG. 2 and, concurrently, at a downward angulation of about thirty degrees relative to said front-to-rear horizontal plane 24 (the XY plane) which is shown in FIG. 1. It is noted that each of said angulations may be in the range of fifteen to forty degrees.

Further, it is to be noted that the pins and bores to the right side of the X axis in FIG. 2 are a mirror image of those to the left side thereof.

As may be seen in FIG. 4, the innermost surfaces of said offsets 38 and 40 constitute the only area of contact between the 10 implant and mandible 11. Accordingly, the interface between the implant and mandible is minimized. Resultingly, a process known as bone re-absorption, which normally occurs at the bone-implant interface, is minimized while the structure of offsets 38 and 40 with their respective bores and mounting pins, as above described, operate to markedly reduce the possibility of implant displacement due to implant contact, facial muscle animation, and external pressures and forces. Thus, it has been found that the above-described angulation of bores 42 and 44 relative to the chin will provide a highly stable positioning of the implant relative to the chin.

With respect to the specific structure of the inventive chin implant, it may, with reference to FIG. 4, be noted that the outer portion 17 of the implant is formed of a soft silastic, low durometer material while said inner portion 15 is formed of a harder higher duron eter silastic material. In a preferred embodiment, silicone is employed as both materials, however, the outer portion 17 is made of a lower durometer material which, in terms of resiliency to touch, resembles the natural fat pad of the human chin.

The distance along the Y-axis in the XY plane between opposite ends of implant 10 is defined by said total included angle 19. In units of length this distance is between 51 and 56 mm.

The length along the Z-axis in the XZ plane is about 12 mm.

The radial width along the X-axis in the XZ plane, between said inner and outer radii 14 and 34, is between 23 and 29 mm.

With further reference to FIG. 4, inner portion 15 is seen to optionally include a longitudinal notch 48 by which radial bending of the implant during securement to the chin may be facilitated.

In construction, each of said outer and inner portions 17 and 15 respectively are formed independently and then bonded together at interface 46 using any of a number of commonly available polymer adhesives. It has been determined that a so-called dual durometer bone implant will provide a prosthetic chin having a tensile property which is more realistic to the touch and, as well, an implant having, along the inner radius 14 thereof, a structure for contact of the periostium of the chin that will minimize adsorption of the implant by the bone. The actual value of the durometer of said inner portion 15 is 40 and that of outer portion 17 is 10.

It is noted that there may be provided an intermediate portion, between said portions 15 and 17, having an intermediate durometer value, e.g., about 28. See FIG. 5.

Accordingly, while there has been shown and described the preferred embodiment of the present invention, it is to be appreciated that the invention may be embodied otherwise than is herein specifically illustrated and described and that, within the scope of such embodiments, certain changes may be made in the detail and construction of the parts without departing from the underlying idea of principles of this invention within the scope of the claims appended herewith.

Having thus described my invention, what I claim as new, useful and non-obvious and, accordingly, secure by Letters Patent of the United States is:

1. A chin implant for augmentation of a human mandible, comprising:
   (a) a biocompatible solid crescent-shaped body having an axis of symmetry, the body comprising an inner portion having an inner surface defining an inner radius and an outer portion having an outer surface defining an outer radius, said inner portion defining a solid included angle about said axis of symmetry greater than a solid included angle defined by said outer portion, each of said inner surface and said outer surface tapering bi-laterally to form respective merged surfaces, said inner radius having a radius of curvature slightly smaller than an opposing radius of curvature of an area of the mandible to be augmented said inner portion having an outer surface opposite said inner surface and said outer portion having an inner surface opposite said outer surface, said outer surface of said inner portion and said inner surface of said outer portion being bonded to each other bonded to each other along opposing faces thereof, said outer portion formed of a lower durometer material than said inner portion, said lower durometer material approximating resilience of a fat pad of the human mandible; and
   (b) radially disposed offset means formed integrally with said inner portion of said crescent-shaped body and extending to outwardly from said inner surface of said inner portion to space said inner surface of said inner portion away from the mandible, said offset means including longitudinal bores proportioned for the receipt of surgical securing pins from said outer surface of said outer portion, said longitudinal bores extending linearly through said inner and outer portions of said body.

2. The implant as recited in claim 1 in which said crescent-shaped body defines a solid included angle of between 30 and 65 degrees about said axis of symmetry.

3. The implant as recited in claim 1 in which said inner surface of said inner portion includes a central notch whereby radial flexibility and adjustability of the implant is thereby provided.

4. The implant as recited in claim 2 in which said inner surface of said inner portion includes a central notch whereby radial flexibility and adjustability of the implant is thereby provided.

5. The implant as recited in claim 1 further comprising:
   an intermediate portion secured between said inner and outer portion, said intermediate portion having a durometer between that of said inner and outer portion.

6. The implant as recited in claim 5 in which said crescent-shaped body defines a solid included angle of between 30 and 65 degrees about said axis of symmetry.

7. The implant as recited in claim 5 in which said inner surface of said inner portion includes a central notch whereby radial flexibility and adjustability of the implant is thereby provided.

8. The implant as recited in claim 6 in which said inner surface of said inner portion includes a central notch whereby radial flexibility and adjustability of the implant is thereby provided.

* * * * *